United States Patent [19]
Schmieding

[11] Patent Number: 5,626,613
[45] Date of Patent: May 6, 1997

[54] CORKSCREW SUTURE ANCHOR AND DRIVER

[75] Inventor: Reinhold Schmieding, Naples, Fla.

[73] Assignee: Arthrex, Inc., Naples., Fla.

[21] Appl. No.: 433,974

[22] Filed: May 4, 1995

[51] Int. Cl.$^6$ ............................................. A61B 17/00
[52] U.S. Cl. ........................ 606/232; 606/104; 606/75; 411/425; 24/711.3
[58] Field of Search ........................ 606/232, 104, 606/75, 73, 187; 623/13; 411/999, 392, 395, 411, 424, 425; 24/711.2, 711.3

[56] References Cited

U.S. PATENT DOCUMENTS

| | | | |
|---|---|---|---|
| 3,499,222 | 3/1970 | Linkow et al. | 433/174 |
| 4,632,100 | 12/1986 | Somers et al. | 606/73 |
| 4,917,554 | 4/1990 | Bronn | 411/392 |
| 4,969,892 | 11/1990 | Burton et al. | 606/232 |
| 5,156,616 | 10/1992 | Meadows et al. | 606/232 |
| 5,258,016 | 11/1993 | Di Poto et al. | 606/232 |
| 5,370,662 | 12/1994 | Stone et al. | 606/232 |
| 5,411,506 | 5/1995 | Goble et al. | 606/104 |
| 5,441,502 | 8/1995 | Bartlett | 606/75 |

FOREIGN PATENT DOCUMENTS

| | | | |
|---|---|---|---|
| 0374088 | 6/1990 | European Pat. Off. | |
| 451932 | 10/1991 | European Pat. Off. | 606/73 |
| 402806 | 10/1909 | France | 24/711.3 |
| 1034728 | 8/1983 | U.S.S.R. | 606/224 |
| 11221 | 8/1891 | United Kingdom | 24/711.3 |

*Primary Examiner*—Jeffrey A. Schmidt
*Attorney, Agent, or Firm*—Ostrolenk, Faber, Gerb & Soffen, LLP

[57] ABSTRACT

A corkscrew suture anchor has a spiral-shaped body having a hollow central core, a distal end, and a proximal end. The distal end of the spiral body terminates in a sharp point, and the proximal end of the spiral-shaped body has an eye for receiving suture. The suture anchor expands resiliently during installation, and contracts to securely grip the bone once the installation force is relaxed. A driver for the suture anchor is provided, the driver including a shaft having a central axis, a length, a distal end, and a proximal end. The shaft is provided at its distal end with a stud aligned with the central axis of the shaft, for insertion into the hollow, central axis of the spiral-shaped body of the suture anchor, and a notch disposed adjacent to the stud for driveably engaging the proximal end of the spiral-shaped body. Suture threaded through the suture eye is threaded through the hollow tubular shaft, and an elastic plug pushed into the proximal end of the hollow tubular shaft holds the threaded suture in place under tension.

8 Claims, 2 Drawing Sheets

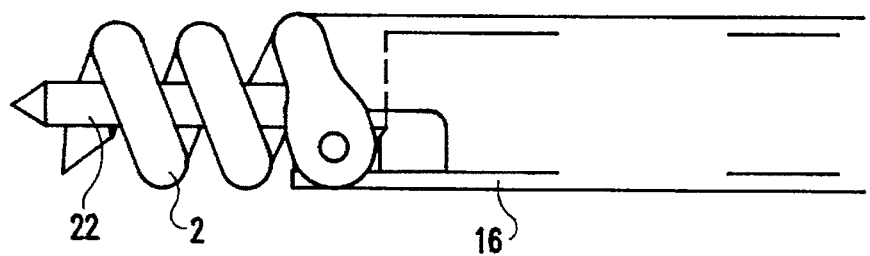
FIG. 8
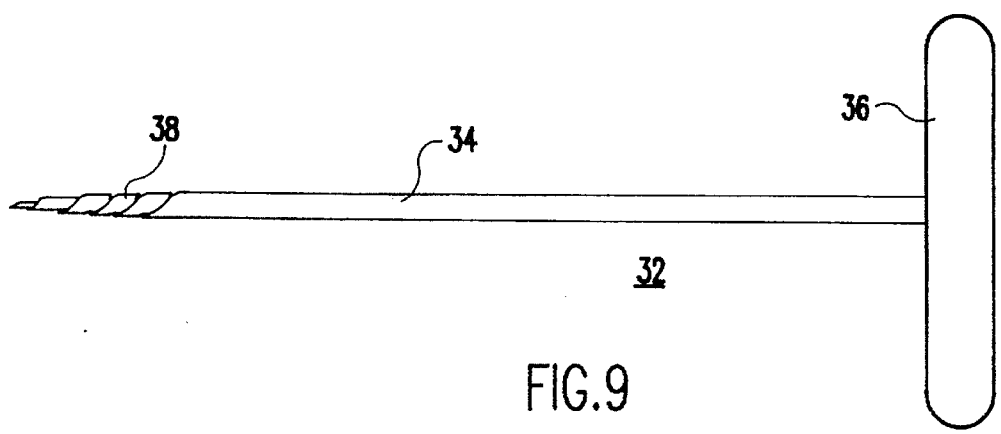
FIG. 9
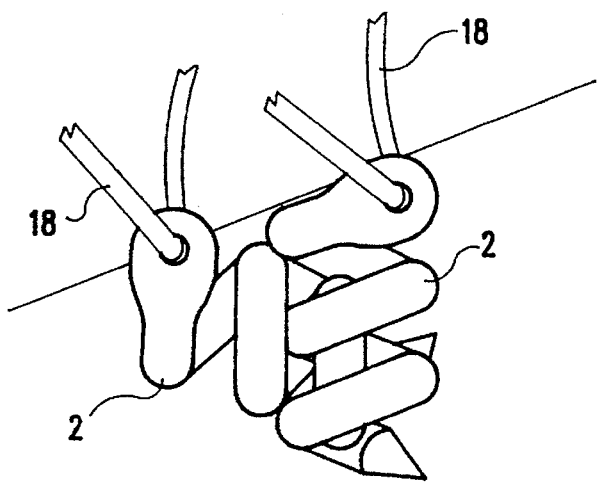
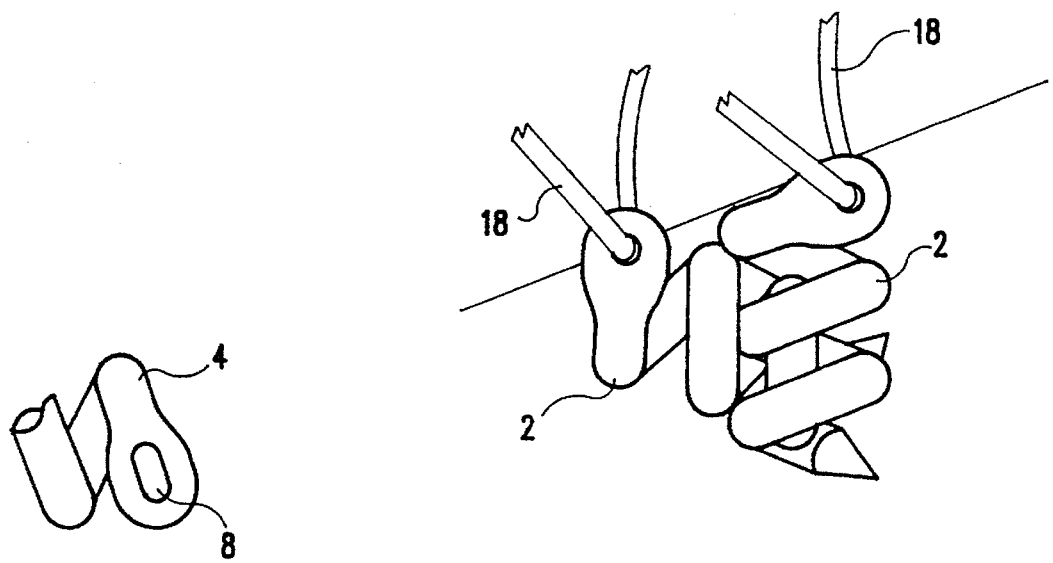
FIG. 3
FIG. 10

CORKSCREW SUTURE ANCHOR AND DRIVER

BACKGROUND OF THE INVENTION

1. Field of the Invention

The present invention relates to an apparatus and method for anchoring suture to bone and, more specifically, to an apparatus and method for anchoring suture using a corkscrew suture anchor.

2. Description of the Related Art

When soft tissue becomes torn away from the bone, reattachment to the bone is necessary. Various devices, such as screws, staples, and sutures alone, have been used to secure soft tissue to bone. Recently, suture anchors have been developed for this purpose.

Among the suture anchors that have been developed, some are self-tapping and others are inserted into a pre-drilled hole. For example, U.S. Pat. No. 4,632,100 discloses a cylindrical suture anchor which includes a drill at a leading end (for boring a hole in a bone) and a flight of threads at a proximal end of the anchor for securing the anchor into the hole created by the drill. U.S. Pat. No. 5,370,662 discloses a self-tapping suture anchor having a flight of threads around a solid body. U.S. Pat. No. 5,156,616 discloses a similar suture anchor having an axial opening for holding a knotted piece of suture.

All of the above-noted suture anchors rely on a flight of threads disposed on the outer surface of a core to secure the anchor to the bone; all provide an easy, secure method of suture fixation in hard cortical bone.

Recent studies indicate, however, that the above-noted suture anchors may have problems related to adequate "pull-out" strength, especially in softer, cancellous bone. Thus, under certain conditions, these known suture anchors can pull out of the bone, requiring costly and difficult repair of the damage site. Moreover, installation of the above-described suture anchors results in a substantial loss of bone stock. Thus, during procedures that require removal or relocation of suture anchors, these types of suture anchors produce holes or defects which reduce bone strength and diminish the availability of specific fixation points.

Accordingly, a need exists for a suture anchor which can be secured in soft cancellous bone and does not displace a large amount of bone upon insertion.

SUMMARY OF THE INVENTION

The suture anchor of the present invention achieves the foregoing objective and overcomes the disadvantages of the prior art by providing a corkscrew suture anchor having a spiral-shaped body. The spiral suture anchor has a hollow central core, a distal end, and a proximal end. The central core typically has a circular cross-section. The distal end of the spiral body terminates in a sharp point, and the proximal end of the spiral-shaped body has a suture eye for receiving suture. The suture eye is formed in a flattened section of the proximal end of the spiral-shaped body. On larger suture anchors, the eye is formed as a slot to allow attachment of more than one piece of suture.

The present invention also provides a suture anchor and driver assembly for driving the corkscrew suture anchor into bone. The corkscrew suture anchor is inserted on the end of the driver. The driver includes a shaft having a central axis, a length, a distal end, and a proximal end. The shaft is provided at its distal end with a stud aligned with the central axis of the shaft, which inserts into the hollow, central axis of the spiral-shaped body of the suture anchor. A notch disposed adjacent to the stud driveably engages the proximal end of the spiral-shaped body. Preferably, the stud has a pointed end. In an alternative embodiment of the invention, the pointed end of the stud extends beyond the sharp point on the distal end of the suture anchor to provide a secure axis around which the suture anchor is driven.

The driver assembly further includes means to hold the corkscrew suture anchor onto the stud. Preferably, the stud is tapered slightly to hold the corkscrew suture anchor onto the stud.

The distal end of the shaft includes a sharp edge for cutting a trough into the bone to allow the suture eye to be driven below the bone surface. Preferably, the sharp edge is located opposite the notch with respect to the central axis of the driver. The shaft includes a tunnel along the length thereof for receiving suture, and a passage is formed between the notch and the tunnel for providing access for suture in the tunnel to the suture eye of the suture anchor.

A suture anchor and driver assembly that can be shipped as a sterile, surgery-ready unit is also provided by the present invention. The suture anchor has suture threaded through the suture eye, and the suture is passed through a passage in the shaft of the driver and up through the hollow tubular shaft. An elastic plug is pushed into the proximal end of the hollow tubular shaft to hold the threaded suture in place under tension.

The present invention also provides a method of anchoring suture in bone using the spiral-shaped suture anchor of the present invention. The method includes the steps of threading suture through the suture eye on the proximal end of the suture anchor, driving the suture anchor under expansion into the bone, and relaxing the expansion on the suture anchor, such that the suture anchor is locked within the bone.

The present invention also provides a method of securing suture by installing two interlocked spiral-shaped suture anchors.

Accordingly, the present invention provides a corkscrew suture anchor with superior pullout strength in soft cancellous bone. Advantageously, the suture anchor of the present invention allows bone ingrowth into the anchor after implantation to increase pullout strength over time. In addition, when removal of the suture anchor is necessary, the corkscrew suture anchor of the present invention minimizes loss of bone stock.

Other features and advantages of the present invention will become apparent from the following description of the invention which refers to the accompanying drawings.

BRIEF DESCRIPTION OF THE DRAWINGS

FIG. 3 is a partial view of the suture anchor of the present invention having a suture eye slot for accommodating more than one piece of suture.

FIG. 8 is a detail view of the suture anchor of the present invention inserted on the shaft of an alternative preferred embodiment of a suture anchor driver according to the present invention.

FIG. 9 is a side view of an easy-out used in removing the suture anchor of the present invention.

FIG. 10 shows the interlocked installation of two suture anchors of the present invention.

DETAILED DESCRIPTION OF THE PREFERRED EMBODIMENTS

Figure 1:
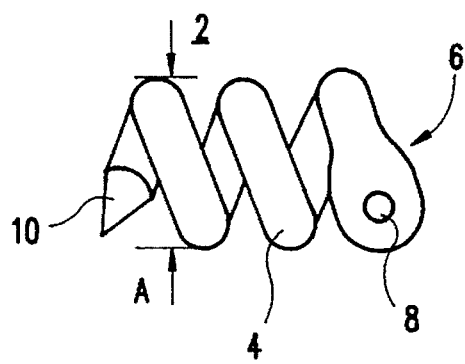
FIG. 1 is a side view of a corkscrew suture anchor according to a preferred embodiment of the present invention.
Figure 2:
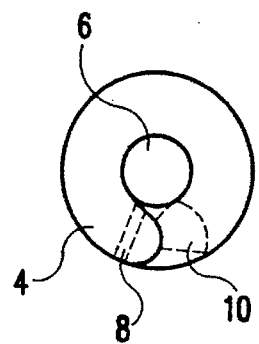
FIG. 2 is an end view of a corkscrew suture anchor according to a preferred embodiment of the present invention.

Referring to FIGS. 1 and 2, the suture anchor 2 of the present invention includes a body 4 provided in the shape of a clockwise helix with a hollow, central core 6. The body is preferably formed of a biocompatible material such as stainless steel. The central core preferably is circular in cross-section, as shown in FIG. 2.

A suture eye 8 is located on a proximal end of helical body 4. Advantageously, suture eye 8 is formed in a position at the end of the helical body where the body flattens out, thus leaving the hollow core unobstructed for insertion of a driving means described more fully below. Helical body 4 is provided with a sharp point 10 at its distal end for piercing bone tissue during the insertion process, described below.

Suture anchor 2 preferably is provided in a variety of sizes and shapes. The following table shows some preferred outside diameters (O.D., A, FIG. 1) and wire sizes:

| O.D. | Wire Size |
| --- | --- |
| 2.5 mm | .032 |
| 3.5 mm | .045 |
| 5.0 mm | .065 |
| 6.5 mm | .085 |

Typically, the 2.5 mm anchor is used for arthroscopic procedures, and can be installed using a hollow, cannulated grasper as described in U.S. Pat. No. 5,466,243, the disclosure of which is herein incorporated by reference. The larger sized suture anchors are advantageous for open surgical procedures, such as open rotator cuff repair, as described in U.S. application Ser. No. 08/288,228 now U.S. Pat. No. 5,575,801. The suture eye 8 on each of the two largest sizes preferably is formed as a slot, as shown in FIG. 3, for holding two or more pieces of braided suture.

The outside diameter of the suture anchor of the present invention is generally three times the wire diameter. Accordingly, hollow central core 6 is approximately equal in diameter to the diameter of the wire used to make the suture anchor.

In the preferred embodiment of the invention, body 4 has three flights or turns between the proximal end and the distal end. Larger sizes of the suture anchor have more flights. Adjacent sections of each flight are separated by a gap that is determined by the number of turns per inch, or pitch, of the suture anchor. Generally, the pitch will be lower as the wire diameter gets larger. For example, a 5 mm suture anchor preferably has 8 turns per inch, or 8 pitch. A 6.5 mm suture anchor typically would have 6 pitch.

Sharp point 10 on the distal end of suture anchor 2 is adapted to pierce the bone and to lead the helical body 4 as the suture anchor forms a helical tunnel in the bone. Helical body 4 preferably is formed of a resilient material, such as wire, so that helical body 4 radially expands, and the spacing between flights increases, as the suture anchor is driven into the bone.

Once the driving torque on the resilient body is relaxed, the suture anchor tends to return to its original diameter, which is smaller than that of the tunnel formed by the expanded screw during insertion, and the spacing between flights tends to return to a normal, smaller size, compressing bone material between the flights. Accordingly, the corkscrew suture anchor becomes securely locked within the bone.

Referring now to FIGS. 4–7, a suture anchor driver 12 is shown. Driver 12 is formed of a hollow, tubular shaft 16 which is provided, at its proximal end, with a cannulated handle 14. Shaft 16 has an outer diameter D which is approximately equal to the outer diameter A of the screw to be inserted. Thus, different drivers are provided for different sizes of screws.

In use, suture anchor 2 is inserted on the distal end of shaft 14, with suture 18 threaded through suture eye 8 and passing through hollow tubular shaft 16 and cannulated handle 14. The ends of suture 18 are accessible to the surgeon outside the proximal end of handle 14. An elastic plug 20 is provided for insertion into the proximal end of the driver to hold the suture under tension.

Figure 5:
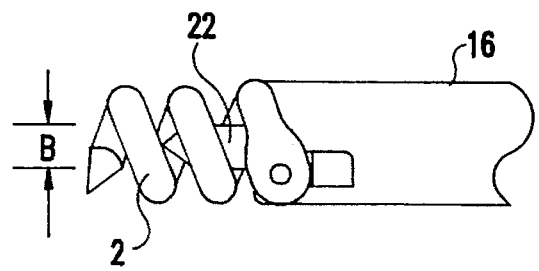
FIG. 5 is an detail view of the suture anchor of the present invention inserted on the shaft of a suture anchor driver.
Figure 7:
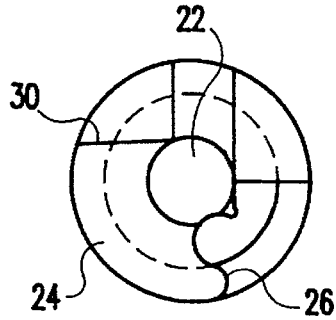
FIG. 7 is an end view of the distal end shown in FIG. 6.

FIG. 5 shows an enlarged view of suture anchor 2 inserted on the distal end of driver 12. A stud 22 extending from the distal end of driver 12 fits within hollow core 6 of suture anchor 2. Suture anchor core 6 has a diameter B adapted to fit securely over stud 22 as described more fully below.

Figure 6:
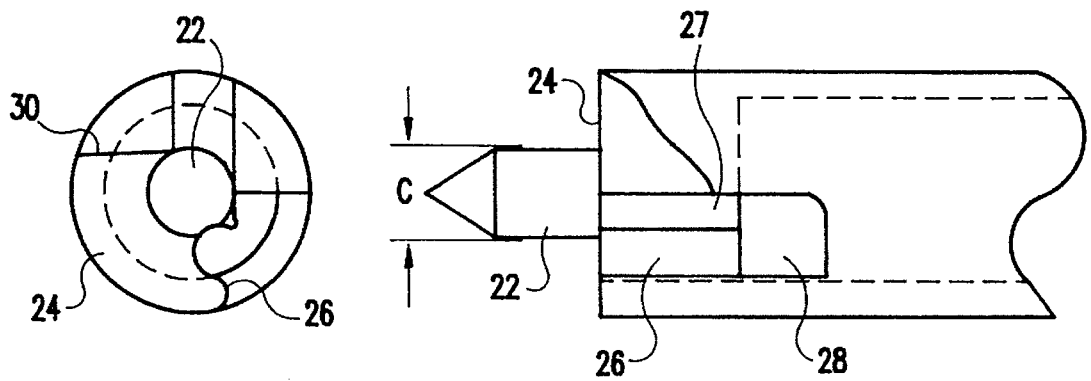
FIG. 6 is a detail view of the distal end of the drive shaft of a suture anchor driver according to a preferred embodiment of the present invention.

As shown in greater detail in FIG. 6, the distal end of driver 12 includes a face 24 from which stud 22 extends. Stud 22 preferably is provided with a slight mortise taper, and has a maximum diameter C that is slightly larger than the internal diameter B of the helical body core 6. Thus, the suture anchor is held onto stud 22 by friction, and by the resilient spring action of the helical body. The stud preferably is provided with a conical point to assist in aligning the driver with the core of the suture anchor.

Figure 4:
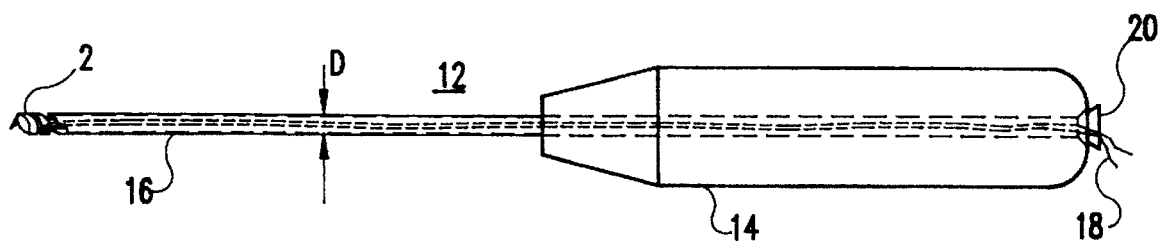
FIG. 4 is a side view of a threaded suture anchor assembly including a suture anchor and driver according to a preferred embodiment of the present invention.

In the embodiment of the invention shown in FIGS. 4 and 5, stud 22 extends only partially through the length of inserted suture anchor 2. In an alternative embodiment, shown in FIG. 8, stud 22 extends beyond the end of inserted suture anchor 2. In this case, the sharp point of stud 22 provides a secure axial position around which the suture anchor is driven. This feature of the driver is especially useful when installing the suture anchor in hard, cortical bone.

Driver 12 is also provided at its distal end with a driving notch 26 for engaging the helical body 6 of suture anchor 2 near suture eye 8. A passage 28 is formed at the proximal end of notch 26 to allow the suture to pass to the inside of hollow, tubular shaft 16. A groove 27 is formed in the notch between face 24 and passage 28 to accommodate suture threaded through suture eye 8.

Face 24 of shaft 16 advantageously includes a sharp edge 30 for cutting a trough into the surface of the bone to allow the suture eye 8 to be driven below the bone surface.

The suture anchor of the present invention is designed for permanent installation. The anchor can be removed, if necessary, with an easy-out 32, as shown in FIG. 9. Easy-out 32 is formed of a shaft 34 which is provided, at its proximal end, with a handle 36, and at its distal end, with a tapered, reverse-threaded screw 38. Twisting easy-out 32 into the center core of suture anchor 2 in a counter-clockwise fashion secures tapered screw 38 within the suture anchor and allows backing the suture anchor out of the insertion site.

FIG. 10 shows two interlocked suture anchors installed such that the flights of each suture anchor interlock.

Increased pull out strength is provided for both suture anchors by installing the suture anchors with interlocking flights in this manner.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A suture anchor and driver assembly for driving a corkscrew suture anchor into bone, comprising:

a suture anchor comprising a spiral-shaped body having a hollow central core, a distal end, and a proximal end, the distal end of the spiral body terminating in a sharp point, and the proximal end of the spiral-shaped body being provided with an eye for receiving suture; and a driver including:

a shaft having a central axis, a length, a distal end, and a proximal end, the shaft being provided at its distal end with:

(i) a stud aligned with the central axis of the shaft, for insertion into the hollow, central axis of the spiral-shaped body of the suture anchor; and (ii) a notch disposed adjacent to the stud for driveably engaging the proximal end of the spiral-shaped body of the suture anchor; and (iii) a sharp edge for cutting a trough into the bone to allow the suture eye of the suture anchor to be driven below the bone surface.

2. The driver assembly of claim 1, wherein the stud has a pointed end.

3. The driver assembly of claim 2, wherein the pointed end of the stud extends beyond the sharp point on the distal end of the suture anchor.

4. The driver assembly of claim 1, further comprising means to hold the corkscrew suture anchor onto the stud.

5. The driver assembly of claim 4, wherein the stud is tapered for holding the corkscrew suture anchor onto the stud.

6. The driver assembly of claim 1, wherein the sharp edge is located opposite the notch with respect to the central axis of the driver.

7. A method of anchoring suture in bone using a spiral-shaped suture anchor having a central axis, a distal end and a proximal end, a sharp point disposed on the distal end of the spiral-shaped suture anchor, and a suture eye disposed on the proximal end of the suture anchor, the method comprising the steps of:

(a) threading suture through the suture eye on the proximal end of the suture anchor;

(b) driving the suture anchor under torqued expansion into the bone; and (c) relaxing the expansion on the suture anchor such that the suture anchor is locked within the bone.

8. A method of anchoring suture in bone using first and second spiral-shaped suture anchors, each suture anchor having a plurality of screw flights, a central axis, a distal end and a proximal end, a sharp point disposed on the distal end of the spiral-shaped suture anchor, and at least the first suture anchor having a suture eye disposed on the proximal end of the suture anchor, the method comprising the steps of:

(a) threading suture through the suture eye on the proximal end of the first suture anchor;

(b) driving the first suture anchor under torqued expansion into the bone at a first position;

(c) relaxing the expansion on the first suture anchor such that the first suture anchor is locked within the bone at the first position; and (d) driving the second suture anchor under torqued expansion into the bone at a second position such that at least one of the plurality of screw flights on the second suture anchor interlocks with at least one of the plurality of screw flights on the first suture anchor.

* * * * *